(12) United States Patent
Haruyama

(10) Patent No.: US 8,124,418 B2
(45) Date of Patent: Feb. 28, 2012

(54) METHOD FOR ELECTROCHEMICALLY MEASURING PHOSPHORIC ACID AND/OR PHOSPHATE

(75) Inventor: Tetsuya Haruyama, Kitakyusyu (JP)

(73) Assignee: Japan Science and Technology Agency, Kawaguchi-Shi Saitama (JP)

( * ) Notice: Subject to any disclaimer, the term of this patent is extended or adjusted under 35 U.S.C. 154(b) by 82 days.

(21) Appl. No.: 11/630,326

(22) PCT Filed: May 24, 2005

(86) PCT No.: PCT/JP2005/009445
§ 371 (c)(1), (2), (4) Date: May 18, 2007

(87) PCT Pub. No.: WO2006/001148
PCT Pub. Date: Jan. 5, 2006

(65) Prior Publication Data
US 2008/0014647 A1    Jan. 17, 2008

(30) Foreign Application Priority Data
Jun. 25, 2004    (JP) ................... 2004-188609

(51) Int. Cl.
*G01N 27/416* (2006.01)
*G01N 27/49* (2006.01)

(52) U.S. Cl. ..... 436/103; 429/422; 435/6.11; 435/287.2

(58) Field of Classification Search .......... 436/103; 429/21, 422; 435/6.11, 287.2
See application file for complete search history.

(56) References Cited

U.S. PATENT DOCUMENTS 6,939,640 B2 * 9/2005 Kourtakis ................ 429/40
7,267,986 B2 * 9/2007 Yukimasa et al. ............ 436/34
2002/0081588 A1 * 6/2002 De Lumley-woodyear et al. ........................ 435/6

FOREIGN PATENT DOCUMENTS

| EP | 1 378 575 A1 | 1/2004 |
| JP | 2-118445 A | 5/1990 |
| JP | 02-118445 A | 5/1990 |
| JP | 11-281616 A | 10/1999 |
| JP | 1128616 A | 10/1999 |
| WO | WO-02/25262 A1 | 3/2002 |
| WO | WO-03/078060 A1 | 9/2003 |

OTHER PUBLICATIONS

Sislberberg et al., Chemistry. (2000) The McGraw Hill Companies. (776).*
Bessiere, J., Tahani, N., & Louis, C.(1994). Concentrated Phosphoric Acid Solutions Neutralized by Sodium Hydroxide: Acid-Base, Oxidation-Reduction, and Solvation Properties. Journal of Chemical Engineering Data.39:381-383.*

(Continued)

*Primary Examiner* — Krishnan S Menon
*Assistant Examiner* — Rebecca M Fritchman
(74) *Attorney, Agent, or Firm* — Birch, Stewart, Kolasch & Birch, LLP

(57) ABSTRACT

Disclosed is a method for measuring a phosphoric acid and/or a phosphate in a sample simply and rapidly with high sensitivity. Specifically disclosed is a method for electrochemically measuring a phosphoric acid and/or a phosphate ester, which is characterized by measuring $PO_4^{3-}$ produced through a chemical reaction of a phosphate, more specifically by measuring the redox response current between $PO_4^{3-}$ and $HPO_4^{2-}$.

16 Claims, 3 Drawing Sheets

OTHER PUBLICATIONS

Mizutani et al., "Amperometric determination of pyruvate, phosphate and urea using enzyme electrodes based on pyruvate oxidase-containing poly(vinyl alcohol)/polyion complex-bilayer membrane," Electrochimica Acta, vol. 45, 2000, pp. 2945-2952.

Ikeno et al., "Biological phosphate ester sensing using an artificial enzyme PMP complex," Sensors and Actuators B, vol. 108, 2005, pp. 608-612.

* cited by examiner

METHOD FOR ELECTROCHEMICALLY MEASURING PHOSPHORIC ACID AND/OR PHOSPHATE

FIELD OF THE INVENTION

The invention relates to a method for an electrochemical measurement of the concentration of phosphoric acid and/or phosphate esters.

BACKGROUND ART

The phosphate esters include many kinds of substances that have an important role in a body, for example, nucleotides such as adenosine-3'-triphosphate (ATP); nucleic acids such as deoxyribonucleic acid (DNA) and ribonucleic acid (RNA); and metabolites such as glycerol phosphoric acid and glucose phosphoric acid. It is therefore very important to measure them in the fields of environment, medicine, clinical inspection, food hygiene and biological research.

As a lot of the nucleotides such as ATP are comprised in contaminants such as microorganisms or food residuum, they are also suitable as an index for the degree of contamination in food factory or kitchen. Proteins, sugars, ATP, etc. have been used for the inspection of the contamination. However, proteins or sugars are not sufficient in sensitivity, and there are contaminants that hardly contain them. A simple luminescence method with an enzyme (luciferase) has been used for the detection of ATP. However, the reagents used in the luminescence method (luciferase and luciferin) are expensive, and an expensive apparatus is also required for this method.

Pyrophosphoric acid, a compound consisting of two phosphoric acids connected via an ester bond, has been used as an index of a reaction amount of DNA polymerase reaction in gene diagnosis and the like. As a method for the detection of pyrophosphoric acid, there are, for example, coloring and luminescence methods using precipitation reaction with calcium and magnesium ions and enzymes. However, as these methods are low in sensitivity and require complex procedures, they are not suitable for automation of a detecting apparatus or a sequential monitoring. Accordingly, the development of a simple method for their detection is needed.

Furthermore, a chemical substance comprising phosphate ester includes organic phosphorus agricultural chemicals such as tetraethyl pyrophosphoric acid. Other organic phosphorus agricultural chemicals such as parathion and malathion have a similar structure with that of phosphate ester. As these organic phosphorus agricultural chemicals are very important substances as a subject of the detection, a method or apparatus for their detection is considered very useful as well. Although gas- or liquid-chromatography has been used for their detection, they will require huge facilities and a lot of money. It is therefore required to develop a simple and inexpensive sensor and method for their detection.

As mentioned above, among the methods for the detection of phosphate ester is known the enzyme luminescence method, which requires, however, expensive reagents and apparatus. The methods for the detection of other phosphate esters depend on instrumental analysis such as HPLC. Accordingly, there is no method that can be applied to in situ detection.

On the other hand, ion-chromatography, atomic absorption methods. Etc. have been used for the detection of the concentration of phosphoric acid in a sample. However, as these methods require a sufficient purification of the sample and an expensive and big-scale apparatus, they are not suitable for the in situ detection. Although a simple ion sensor using ionophore is also known, it has a low selectivity especially for phosphoric acid, and would be difficult to use for the detection in a practically low concentration range.

Patent Document 1 discloses an invention relating to a support catalyzing chemical reaction of chemical substances, which comprises the combination of metal ions and a polymer whose structure is determined by coordination with the metal ions, or the combination of metal ions, a polymer which functions to hold the metal ions, and a polymer having electron-attracting functional groups. As one example of the application of such support is described a method for the detection of phosphate ester.

Specifically, the above patent document discloses an example for the detection of ATP, TDP and pyrophosphoric acid. However, all of these substances are detected by reduction currency (minus currency) obtained at +100 mV. This currency is derived from electrochemically reductive dissociation of a complex comprising Cu in an artificial enzyme, which is coordinated with "P" of phosphate ester.

[Patent Document 1] WO03/078060 A1 pamphlet

DISCLOSURE OF THE INVENTION

Problems to be Solved by the Invention

The problem to be solved by the present invention is therefore to provide a method that enables to simply and rapidly detect a phosphoric acid and/or a phosphate ester in a sample.

Means for Solving the Problems

It has been known that most of the phosphoric acid in aqueous solution is stable in equilibrium between $HPO_4^{2-}$ (49.9973%) and $H_2PO_4^-$ (49.9973%), and that there are a very tiny amount of $H_3PO_4$ (0.00039%) and $PO_4^{3-}$ (0.00016%). The present inventor has found, however, that the phosphoric acid will transiently exist as $PO_4^{3-}$ for a short period of time in a state that can be electrochemically detected only just after dephosphorylation or hydrolysis reaction and before reaching the above equilibrium wherein $HPO_4^{2-}$ and $H_2PO_4^-$ (neither of which can not be electrochemically detected) account for 99.99%. As a result, the inventor has also found that $PO_4^{3-}$ can be quantitatively measured by measuring reduction current due to the electrochemical reduction of $PO_4^{3-}$ and/or by measuring oxidation current due to the electrochemical oxidation of $HPO_4^{2-}$, i.e., the reduction product of $PO_4^{3-}$. By carrying out two electrode reactions vice versa, a total current amount will be doubled, increasing the sensitivity of the detection. The present invention has been completed on the basis of the above findings.

Accordingly, by appropriately arranging a catalyst (natural or artificial enzyme) involved in dephosphorylation reaction and an electrode system, phosphoric acid released by the dephosphorylation reaction will reach the surface of an electrode in the state of $PO_4^{3-}$ or $HPO_4^{2-}$, and then be oxidized or reduced at the electrode potential, making it possible to quantitatively measure the phosphoric acid and/or phosphate ester by measuring a response current thereby.

The present invention is therefore related to the following aspects.

1. A method for electrochemically measuring a phosphoric acid and/or a phosphate ester, characterized by measuring $PO_4^{3-}$ generated by a chemical reaction of the phosphoric acid and/or the phosphate ester.
2. A method according to Claim 1 wherein the chemical reaction is dephosphorylation or hydrolysis reaction.

3. A method according to Claim 2 wherein a redox response current between $HPO_4^{2-}$ and $PO_4^{3-}$ is measured.
4. A method according to Claim 3 wherein the redox response current is obtained by applying a constant potential in the range of less than +100 mV.
5. A method according to Claim 4 wherein a reduction current of $PO_4^{3-}$ is obtained by applying a constant potential in the range of less than −50 mV.
6. A method according to Claim 5 wherein the reduction current of $PO_4^{3-}$ is obtained by applying a constant potential of −250 mV.
7. A method according to Claim 4 wherein an oxidation current of $HPO_4^{2-}$ is obtained by applying a constant potential in the range of +50 mV or more.
8. A method according to any one of Claims 1-7 wherein the phosphoric acid is esterified and $PO_4^{3-}$ generated by a chemical reaction of the phosphate ester thus obtained is measured.
9. A method according to any one of Claims 1-7 wherein $PO_4^{3-}$ generated by deprotonation of the phosphoric acid is measured.
10. A method according to any one of Claims 1-9 wherein the chemical reaction is carried out with a catalyst.
11. A method according to Claim 10 wherein the catalyst is selected from the group consisting of dephosphorylase, phosphate ester hydrolase and an artificial enzyme being able to catalyze the dephosphorylation or hydrolysis reaction.
12. A method according to Claim 11 or 11 wherein the catalyst forms a catalyst layer on the interface of an electrode.

Advantages of the Invention

According to the present electrochemically measuring method, a very tiny amount of the phosphoric acid and/or phosphate ester in the range of about several tens μM~several hundreds μM in the sample can be simply and rapidly measured in situ.

BEST MODE FOR CARRYING OUT THE INVENTION

Figure 1:
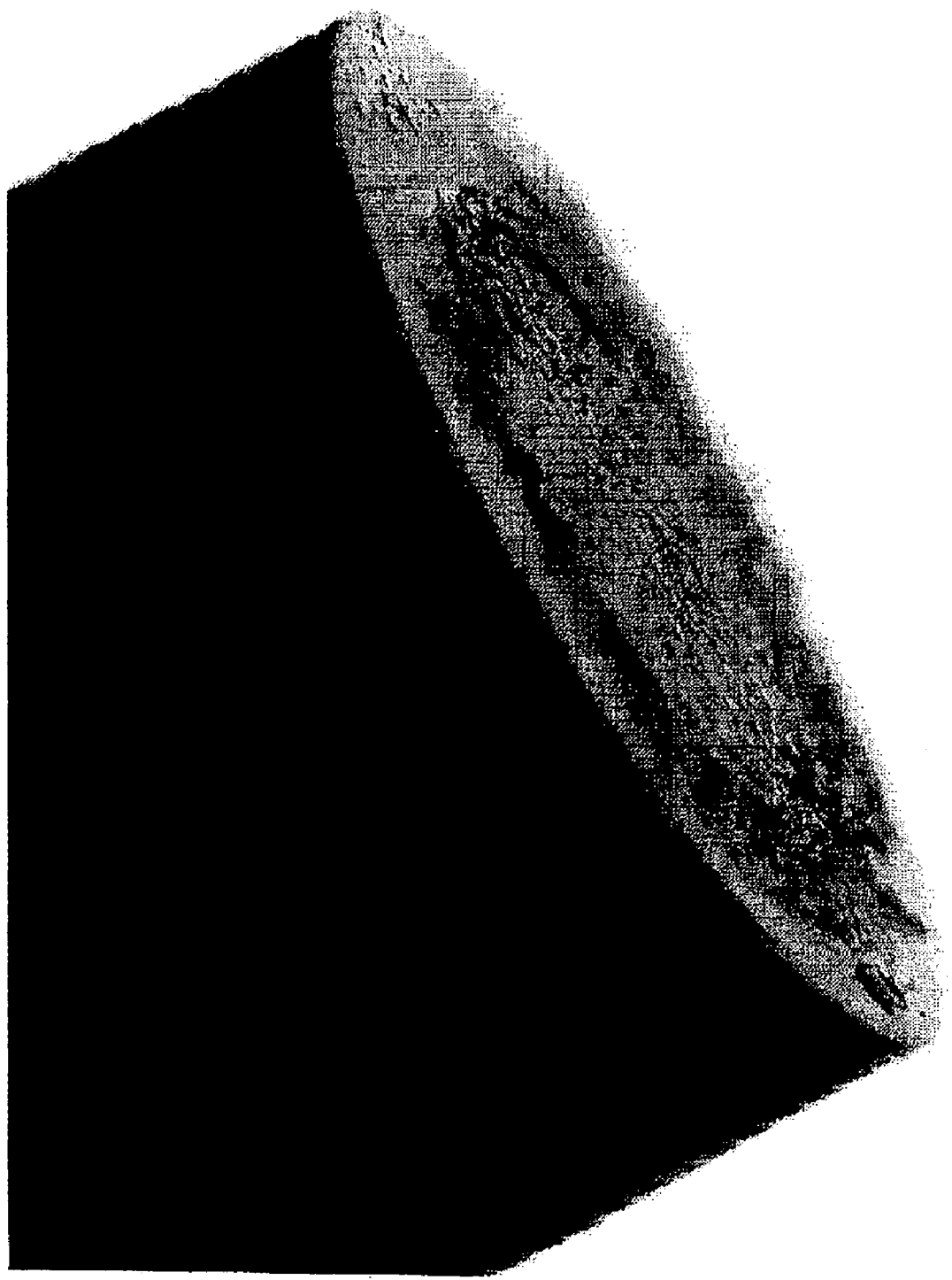
FIG. 1 shows an enlarged photo (magnification: ×50) of the reaction face (a catalyst layer on the surface of the electrode) of a sensor device manufactured in Example 1.

The "phosphate ester," a subject of the measurement of the present invention includes any compounds known for those skilled in the art such as those described in "Background Art" of the present specification. The chemical reaction may include any one as long as it can generate $PO_4^{3-}$ from the phosphate ester. Such reaction may preferably be catalyzed by an enzyme and the like in view of reaction efficiency and conditions, not excluding one without using the catalyst.

Examples of the reaction are dephosphorylation and hydrolysis. Accordingly, an enzyme that may be used in the present invention includes dephosphorylases that catalyze the dephosphorylation reaction by hydrolyzing a monoester bond of the phosphoric acid in a biological molecule, which are called "phosphatase" derived from various organisms, and phosphate ester hydrolases that catalyze the hydrolysis of an ester bond of the phosphoric acid between β-phosphorus and γ-phosphorus of ATP, which are called "ATPase" and any artificial enzymes known for those skilled in the art, which can catalyze the dephosphorylation or hydrolysis reaction.

One of the examples of the above artificial enzymes is the catalyst support disclosed in the WO03/078060 A1 pamphlet. Such catalyst may be comprised in the catalyst layer formed in the interface of the electrode in any manner known for those skilled in the art.

In the present invention, the measurement of $PO_4^{3-}$ generated by the chemical reaction may be preferably done by measuring the redox response current between $HPO_4^{2-}$ and $PO_4^{3-}$. The reduction current of $PO_4^{3-}$ may be obtained by applying a constant potential in the range of less than +100 mV, preferably less than −50 mV, more preferably at −250 mV. The oxidation current of $HPO_4^{2-}$ may be obtained by applying a constant potential in the range of +50 mV or more.

In the present invention, after the phosphoric acid is esterified in any way known for those skilled in the art, and $PO_4^{3-}$ generated by a chemical reaction of the phosphate ester thus obtained may be measured. Alternatively, $PO_4^{3-}$ generated by deprotonation of the phosphoric acid may be measured.

The present invention may be carried out with any electrochemically measuring apparatus or instrument known for those skilled in the art. For examples a two-, or three-electrode system is constructed in the sample wherein an appropriate enzyme is subjected to the surface or interface of the electrode, and the constant potential applied for the measurement. Such two-, or three-electrode system may be formed by any method known for those skilled in the art.

EXAMPLE

The present invention will be explained in detail with reference to the examples. The technical scope of the present invention shall not be limited in any way by the examples.

Example 1

Quantitative Electrochemical Measurement of Pyrophosphoric Acid (Sensor for Pyrophosphoric Acid)

Pyrophosphoric acid, a kind of the phosphate esters, was measured using an artificial enzyme as a catalyst for dephosphorylation of the phosphate ester. The artificial enzyme is described in WO03/078060 A1 pamphlet as the catalyst support that catalyzes dephosphorylation of the phosphate ester.

Specifically, the artificial enzyme was prepared as follows. $CuCl_2$ (200 mM) was dissolved in aqueous solution of hydrochloric acid (a final concentration of 40 mM) and to this solution was added 20 mM polyhistidine (Sigma) while being neutralized with NaOH solution. The resulting solution was stirred at 25° C. one day with a vortex mixer, mixed with 20 mM polystyrene sulfonic acid (Aldrich Co.) and then stirred for dissolution. The resulting support comprising precipitated metal ions and polymers was used as the artificial enzyme. The artificial enzyme was thinned on the surface of a platinum electrode (5 mm×5 mm×0.1 mm) to give a sensor device for pyrophosphoric acid (FIG. 1).

Figure 2:
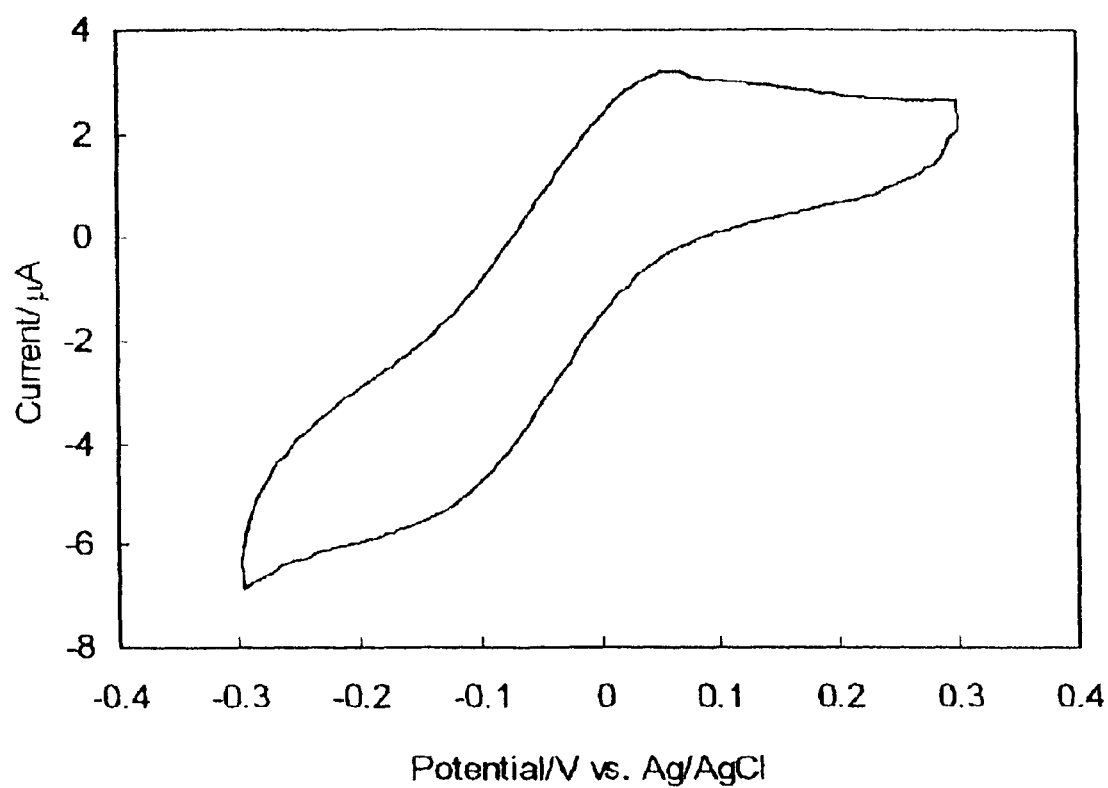
FIG. 2 is a graph showing a current vs. potential curve showing current response obtained by potential scan in the range of −400 mV~+400 mV (vs. AgAgCl).

By using an electrochemically measuring apparatus (HOKUTO DENKO Corporation: HZ-3000 system) consisting of a three-electrode system (platinum counter electrode, AgAgCl reference electrode) comprising the sensor device soaked in a buffer containing 50 mM of pyrophhosphoric acid, the potential scan was carried out in the range of −400 mV~+400 mV (vs. AgAgCl) with the application of potential and current response was recorded. As a result, the redox current response was obtained around −100 mV (vs. Ag/AgCl), as shown in FIG. 2. The results mean that the reduction and oxidation between $HPO_4^{2-}$ and $PO_4^{3-}$ occurred on the surface of the electrode.

More specifically, FIG. 2 demonstrates that the reduction current (minus current) of $PO_4^{3-}$ was obtained by applying a constant potential in the range of less than about −50 mV, especially at about −250 mV, and that the oxidation current (plus current) of $HPO_4^{2-}$ was obtained by applying a constant potential in the range of +50 mV or more. In this reaction, the reduction of $PO_4^{3-}$ can be realized only in the range of less than about −50 mV, and the reduction reaction (minus current) will not proceed at all at +100 mV. Accordingly, the redox current response obtained in the present method is based on a mechanism different from that of the electrochemical measurement disclosed in the WO03/078060 A1 pamphlet.

Figure 3:
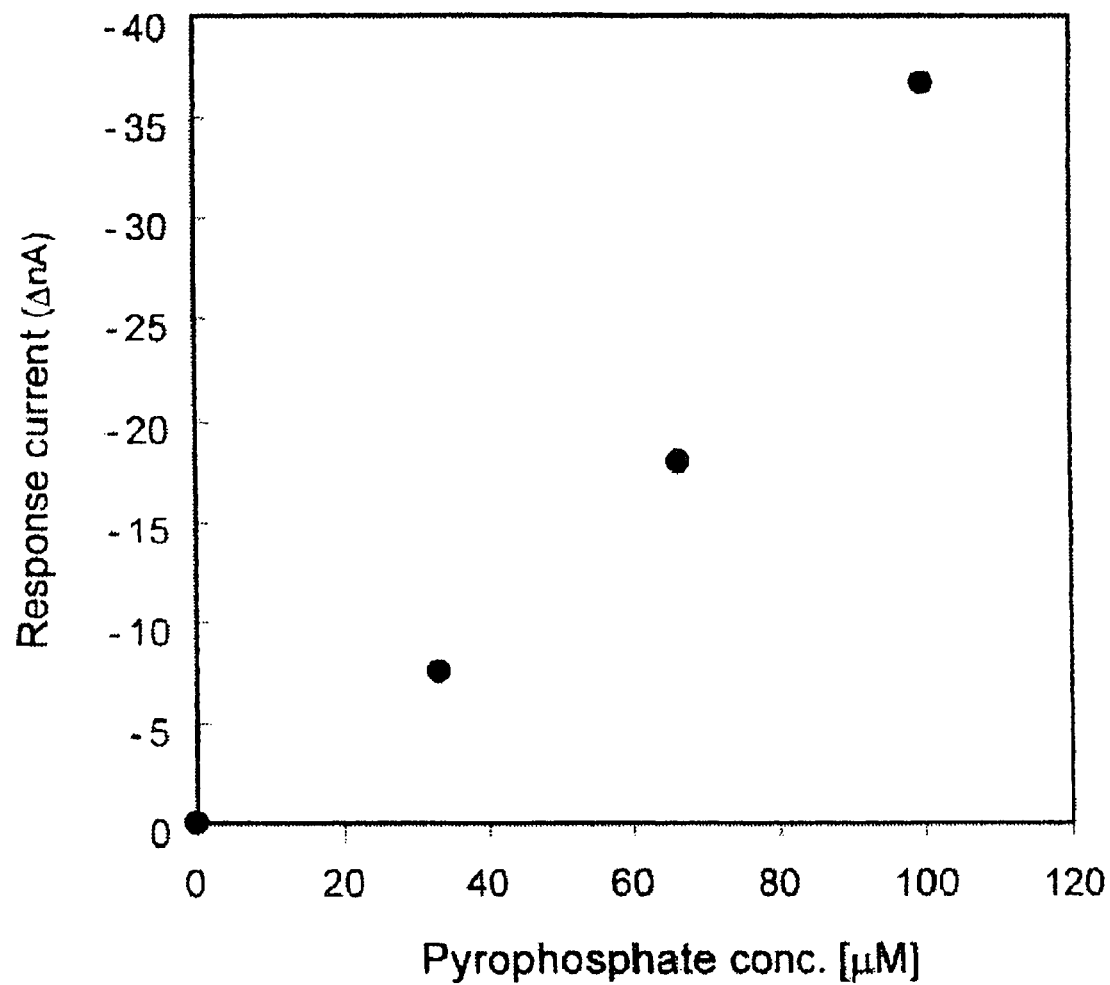
FIG. 3 shows an analytical curve showing the relationship between the concentration of pyrophosphoric acid and a response current from the sensor device in FIG. 1, which was obtained in the electrochemical measurement of the pyrophosphoric acid by said sensor device.

Since it has been found that the dephosphorylation product of pyrophosphoric acid, i.e., $PO_4^{3-}$ was able to be electrochemically reduced at about −250 mV (vs. AgAgCl), the constant potential at −250 mV (vs. AgAgCl) was applied to the sensor device soaked in the buffer. Pyrophosphoric acid was dropped into the buffer with stirring of the buffer with a stirrer, and the reduction response current was obtained in response to the concentration of the pyrophosphoric acid added (FIG. 3)

Industrial Applicability

By the present invention, it is possible to simply and rapidly detect in situ phosphoric acid and/or phosphate esters in a sample. The phosphate esters include biological energetic substances such as ATP and biological informative molecules such as DNA and RNA. Accordingly, the present invention may provide a wide variety of applications as a measuring or detecting means in the filed of environment, medicine, clinical inspection, food hygiene and biological research.

The invention claimed is:

1. A method for electrochemically measuring the concentration of a phosphoric acid and/or a phosphate ester, comprising:
   generating $HPO_4^{2-}$ and $PO_4^{3-}$ by a dephosphorlyation or hydrolysis reaction of the phosphate ester; and
   directly measuring a redox response current between said $HPO_4^{2-}$ and $PO_4^{3-}$.

2. A method according to claim 1, wherein the redox response current is obtained by applying a constant potential in the range of less than +100 mV.

3. A method according to claim 2, wherein a reduction current of $PO_4^{3-}$ is obtained by applying a constant potential in the range of less than −50 mV.

4. A method according to claim 3, wherein the reduction current of $PO_4^{3-}$ is obtained by applying a constant potential of −250 mV.

5. A method according to claim 2 wherein an oxidation current of $HPO_4^{2-}$ is obtained by applying a constant potential in the range of +50 mV or more.

6. A method according to claim 1 wherein the phosphoric acid is esterified and $PO_4^{3-}$ generated by dephosphorylation or hydrolysis reaction of the phosphate ester thus obtained is measured.

7. A method according to claim 1 wherein $PO_4^{3-}$ generated by deprotonation of the phosphoric acid is measured.

8. A method according to claim 1 wherein the dephosphorylation or hydrolysis reaction is carried out with a catalyst.

9. A method according to claim 8 wherein the catalyst is selected from the group consisting of dephosphorylase, phosphate ester hydrolase and an artificial enzyme being able to catalyze the dephosphorylation or hydrolysis reaction.

10. A method according to claim 8 or 9 wherein the catalyst forms a catalyst layer on the interface of an electrode.

11. An apparatus for electrochemically measuring the concentration of a phosphoric acid and/or a phosphate ester, comprising:
    generating $HPO_4^{2-}$ and $PO_4^{3-}$ by a dephosphorlyation or hydrolysis reaction of the phosphate ester; and
    directly measuring a redox response current between said $HPO_4^{2-}$ and $PO_4^{3-}$ containing:
    a catalyst of a dephosphorylation or hydrolysis reaction of a phosphate ester,
       wherein said catalyst forms a catalyst layer on the interface of an electrode.

12. A method for electrochemically measuring the concentration of a phosphoric acid and/or a phosphate ester, comprising:
    generating $HPO_4^{2-}$ and $PO_4^{3-}$ by a dephosphorlyation or hydrolysis reaction of the phosphate ester; and
       measuring a redox response current between said $HPO_4^{2-}$ and $PO_4^{3-}$ generated by the dephosphorylation or hydrolysis reaction in a solution consisting essentially of a buffer, the phosphoric acid and/or the phosphate ester, and optionally includes a catalyst for the dephosphorylation or hydrolysis reaction, which forms a catalyst layer on the interface of an electrode.

13. The method according to claim 12, wherein said solution includes a catalyst for the dephosphorylation or hydrolysis reaction of the phosphate ester, which forms a catalyst layer on the interface of an electrode.

14. The method according to claim 12, wherein said solution does not include a catalyst for the dephosphorylation or hydrolysis reaction of the phosphate ester, which forms a catalyst layer on the interface of an electrode.

15. A method for electrochemically measuring the concentration of a phosphoric acid and/or a phosphate ester, comprising:
    generating $HPO_4^{2-}$ and $PO_4^{3-}$ by a dephosphorlyation or hydrolysis reaction of the phosphoric acid and/or the phosphate ester; and
    directly measuring a redox response current between said $HPO_4^{2-}$ and $PO_4^{3-}$ generated by the dephosphorylation or hydrolysis reaction of the phosphate ester in a solution which consists of a buffer, phosphoric acid and/or the phosphate ester.

16. The method of any one of claim 1, 11, 12, or 15 wherein said phosphate ester to be measured is pyrophosphoric acid.

* * * * *